United States Patent [19]

Bohen

[11] 4,177,187

[45] Dec. 4, 1979

[54] STABILIZERS FOR HALOGENATED RESINS

[75] Inventor: Joseph M. Bohen, King of Prussia, Pa.

[73] Assignee: Pennwalt Corporation, Philadelphia, Pa.

[21] Appl. No.: 828,703

[22] Filed: Aug. 29, 1977

[51] Int. Cl.² .............................................. C08K 5/58
[52] U.S. Cl. ...................... 260/45.75 S; 260/45.7 S; 260/45.7 R; 252/406
[58] Field of Search ................ 260/45.7 S, 45.75 S, 260/45.7 R; 252/406

[56] References Cited

U.S. PATENT DOCUMENTS

| | | | |
|---|---|---|---|
| 2,726,227 | 12/1955 | Leistner et al. | 260/45.75 S |
| 2,888,435 | 5/1959 | Wallace | 260/45.75 S |
| 3,764,571 | 10/1973 | Jennings | 260/45.75 S |
| 3,803,083 | 4/1974 | Brecker | 260/45.75 S |

*Primary Examiner*—V. P. Hoke

[57] ABSTRACT

A mixture of a tin tetrakis (mercaptide) and an overbased organic complex of an alkali or alkaline earth metal base has been found to provide unexpected improvement in the heat stabilization of halogenated resins.

11 Claims, No Drawings

STABILIZERS FOR HALOGENATED RESINS

Tin tetrakis (mercaptides) have been proposed as stabilizers for halogen-containing resins to protect them against degradation by heat during the fabrication of the resin into useful articles. Prior patents which disclose tin tetrakis (mercaptides) and their utility as stabilizers are U.S. Pat. Nos. 2,726,227 and 2,888,435. In commercial practice, however, the tin tetrakis (mercaptides) have not been used as stabilizers because their performance is far inferior to that of organotin mercaptides (characterized by at least one C-Sn bond). In fact, in some cases the tin tetrakis (mercaptides) are found to actually catalyze the decomposition of the halogen-containing resin.

It has been discovered that the performance of tin tetrakis (mercaptides) is significantly improved by the synergistic action of an overbased organic complex of an alkali or alkaline earth metal base. This unexpected synergism provides a novel stabilizer system that is much less expensive and can be substituted for organotin mercaptides in the stabilization of halogenated resins. It has also been discovered that addition of a third component, namely an alkali or alkaline earth metal salt of a mercaptan or mercapto acid further improves performance, especially initial color inhibition.

The tin tetrakis (mercaptides) which are operable in this invention are characterized as having four Sn-S bonds and are described by the formula:

$$R^1S-\underset{\underset{R^4}{\overset{\overset{R^2}{S}}{|}}}{\overset{}{Sn}}-SR^3 \qquad I$$

wherein
$R^1$, $R^2$, $R^3$, and $R^4$ are hydrocarbon radicals (e.g., alkyl, cycloalkyl, aryl, or mixed alkyl-aryl) of 1–22 carbon atoms optionally substituted by halogen, —XH, —XR$^5$, $$-\overset{\overset{Y}{\|}}{C}-R^5-X-\overset{\overset{Y}{\|}}{C}R^5, \text{ or } -\overset{\overset{Y}{\|}}{C}XR^5$$

where $R^5$ is a 1–20 carbon atom alkyl, alkenyl, cycloalkyl, aryl, or mixed alkyl-aryl group and both X and Y are independently selected from oxygen (O) and sulfur (S).

Examples of these tin tetrakis (mercaptides) are:

Sn(SCH$_3$)$_4$

Sn(SC$_4$H$_9$)$_4$
Sn(SC$_{12}$H$_{25}$)$_4$

Sn(S—⟨S⟩)$_4$

Sn(S—⟨⟩)$_4$

Sn(SC$_6$H$_4$-p-CH$_3$)$_4$

Sn(SC$_6$H$_4$-p-Cl)$_4$

Sn(SCH$_2$C$_6$H$_5$)$_4$

Sn(SCH$_2$CH$_2$OH)$_4$
Sn(SCH$_2$CH CH$_2$)$_4$
         | |
        OH OH
Sn(SC$_2$H$_4$O$_2$CC$_6$H$_5$)$_4$

Sn(SC$_3$H$_6$O$_2$CC$_{17}$H$_{33}$)$_4$

Sn(SC$_2$H$_4$O$_2$CC$_{17}$H$_{35}$)$_4$

Sn(SCH$_2$CHCH$_2$O$_2$CCH$_3$)$_4$
      |
      O$_2$CCH$_3$
Sn(SC$_8$H$_{17}$)$_2$8SCH$_2$CO$_2$C$_8$H$_{17}$)$_2$
Sn(SCH$_2$CO$_2$C$_3$H$_7$)$_{2.5}$(SCH$_2$CH$_2$CO$_2$C$_8$H$_{17}$)$_{1.5}$
Sn(SC$_{12}$H$_{25}$)$_2$(SCH$_2$CO$_2$C$_4$H$_9$)$_2$
Sn(SCH$_2$CH$_2$S$_2$CCH$_3$)$_4$
Sn(SC$_2$H$_4$O$_2$CC$_{17}$H$_{33}$)$_4$

Sn(SCH$_2$CHC$_4$H$_9$)$_4$
       |
       C$_2$H$_5$
Sn(SCH$_2$CO$_2$C$_8$H$_{17}$)$_4$
Sn(SCH$_2$CH$_2$CO$_2$C$_8$H$_{17}$)$_4$
Sn(SCHCO$_2$C$_4$H$_9$)$_4$
      |
      CH$_2$CO$_2$C$_4$H$_9$

Sn(SCHCO$_2$C$_2$H$_5$)$_4$
      |
      CO$_2$C$_2$H$_5$ $$\text{Sn(SCH}_2\overset{\overset{O}{\|}}{C}\text{C}_6\text{H}_5)_4$$
Sn(SC$_6$H$_5$)$_{1.5}$(SCHCO$_2$C$_4$H$_9$)$_{2.5}$
          |
          CH$_2$CO$_2$C$_4$H$_9$
$$\text{Sn(SC}_3\text{H}_7\text{S}\overset{\overset{O}{\|}}{C}\text{CH}_3)_4$$
Sn(SCH$_3$)$_3$(SCH$_2$CO$_2$C$_{20}$H$_{41}$)
Sn(SCH$_2$CH$_2$SC$_{10}$H$_{21}$)$_4$ Sn(SCH$_2$CHCH$_2$—Cl)$_4$
       |
       OC$_2$H$_5$
Sn(SCH$_2$CO$_2$C$_4$H$_9$) (SCHCO$_2$C$_4$H$_9$)$_3$
                                |
                                CH$_2$CO$_2$C$_4$H$_9$ Sn(S—⟨S⟩)$_2$(S—⟨⟩)$_2$ Sn(SC$_4$H$_9$) (SCH$_2$CO$_2$C$_8$H$_{17}$)$_3$ Sn(SC$_2$H$_5$)$_2$(SC$_4$H$_9$)$_2$ Sn(SC$_4$H$_9$)$_2$(SCH$_2$CO$_2$C$_8$H$_{17}$)$_2$
Sn(SC$_4$H$_9$)$_3$(SCH$_2$CO$_2$C$_8$H$_{17}$)

Particularly preferred tin compounds are:

| | |
|---|---|
| $Sn(SCH_2CO_2C_8H_{17})_4$ | $Sn(SC_{12}H_{25})_2(SCH_2CO_2C_8H_{17})_2$ |
| $Sn(SC_4H_9)(SCH_2CO_2C_8H_{17})_3$ | $Sn(SCH_2CH_2CO_2C_8H_{17})_4$ |
| $Sn(SC_4H_9)_2(SCH_2CO_2C_8H_{17})_2$ | $Sn(SC_{12}H_{25})(SCH_2CH_2CO_2C_8H_{17})_3$ |
| $Sn(SC_4H_9)_3(SCH_2CO_2C_8H_{17})$ | $Sn(SC_{12}H_{25})_2(SCH_2CH_2CO_2C_8H_{17})_2$ |
| $Sn(SC_{12}H_{25})_4$ | $Sn(SCHCO_2C_4H_9)_4$ |
| | $\quad\quad\quad\mid$ |
| | $\quad\quad CH_2CO_2C_4H_9$ |
| $Sn(SC_{12}H_{25})(SCH_2CO_2C_8H_{17})_3$ | $Sn(SC_{12}H_{25})_2(SCHCO_2C_4H_9)_2$ |
| | $\quad\quad\quad\mid$ |
| | $\quad\quad CH_2CO_2C_4H_9$ |
| $Sn(SC_{12}H_{25})(BSCHCO_2C_4H_9)_3$ | $Sn(SC_2H_4O_2CC_{17}H_{33})_4$ |
| $\quad\quad\mid$ | |
| $CH_2CO_2C_4H_9$ | |
| | $Sn(SC_2H_4O_2CC_{17}H_{35})_4$ |

The tin tetrakis (mercaptides) of this invention can be conveniently prepared by the reaction of selected mercaptans with anhydrous stannic chloride optionally in the presence of an HCl acceptor such as an inorganic or organic base.

The second component of the stabilizer composition of this invention is an overbased organic complex of an alkali or alkaline earth metal base described by the formula:

$$R_n^6 M \cdot x M^1 A_{n'} \quad \quad II$$

wherein:

$R^6$ is a residue of an organic acid selected from carboxylic, thiocarboxylic, sulfonic, sulfinic, phosphonic, phosphinic, thiophosphonic, thiophosphinic, phenolic, and thiophenolic;

n and n' are 1 or 2;

M and $M^1$ are the same or dissimilar alkali or alkaline earth metals (group I and IIa metals of the periodic table);

X is a positive number greater than zero; and,

A is the anion portion of the basic material selected from $OH^{-1}$, $CO_3^{-2}$, $O^{-2}$, $SO_4^{-2}$, $SO_3^{-2}$, $HCO_3^{-1}$, $S^{-2}$.

The organic complex is generally dispersed in a low-volatile liquid such as hydrocarbon oil, a plasticizer, an epoxy ester, or a combination thereof.

The fundamental technique for preparing such overbased complexes involves the preparation of a soap or salt of an organic acid in the presence of an amount of neutralizing agent, such as a metal oxide or hydroxide, which results in the formation of a stable product that contains an amount of metal in substantial excess of that which is theoretically required to replace the acidic hydrogens of the organic acid; e.g., carboxylic, phenolic, sulfonic, sulfinic, etc., used as the starting material. Generally, the stoichiometric excess of metal for the overbased complexes is at least one equivalent, as presently preferred, but can vary from about 0.1–30 equivalents. Also, the reaction product may be treated with an acidic gas (e.g., $CO_2$) to reduce the free basicity of the complex. (The free basicity is regarded as that amount of metal base which is titratable to a pH of about 8; whereas, the total basicity of the complex is titratable to a pH of about 3.)

Detailed descriptions of these overbased organic complexes and the methods by which they are prepared are described in the following U.S. Pats.: U.S. Pat. Nos. 2,616,904; 2,616,905; 2,616,906; 2,616,911, 2,616,924; 2,616,925; 2,617,049; 2,695,910; 2,723,234; 2,767,209; 2,777,874; 2,798,852; 2,839,470; 2,883,340; 2,915,517; 2,959,551; 2,968,642; 2,971,014; 2,989,463; 3,001,981; 3,027,325; 3,108,960; 3,147,232; 3,172,855; 3,194,823; 3,232,883; 3,242,079; 3,242,080; 3,256,186; 3,274,135 and 3,350,308.

The disclosures of these patents relating to overbased organic complexes and the methods for their manufacture are incorporated herein by reference.

As set forth in U.S. Pat. No. 3,764,571, overbased acids wherein the acid is a phosphorus acid, a thiophosphorus acid, phosphorus acid-sulfur acid combination, and sulfur acid prepared from polyolefins are disclosed in U.S. Pat. Nos. 2,883,340, 2,915,517, 3,001,981, 3,108,960, and 3,232,883. Overbased phenates are disclosed in U.S. Pat. No. 2,959,551 while overbased ketones are found in U.S. Pat. No. 2,798,852. A variety of overbased materials derived from oil soluble metal-free, non-tautomeric neutral and basic organic polar compounds such as esters, amines, amides, alcohols, ethers, sulfides, sulfoxides, and the like are disclosed in U.S. Pat. Nos. 2,968,642, 2,971,014 and 2,989,463. Another class of materials which can be overbased are the oil-soluble, nitro-substituted aliphatic hydrocarbons, particularly nitro-substituted polyolefins such as polyethylene, polypropylene, polyisobutylene, etc. Materials of this type are illustrated in U.S. Pat. No. 2,959,551. Likewise, the oil-soluble reaction product of alkylene polyamines such as propylene diamine or N-alkylated propylene diamine with formaldehyde or a formaldehyde producing compound (e.g., paraformaldehyde) can be overbased. Other compounds suitable for overbasing are disclosed in the above cited patents or are otherwise well-known in the art.

A class of particularly suitable organic materials the residue of which may form the $R^6$ group of the above formula for the overbased organic complex include oil-soluble organic acids, preferably those containing at least twelve aliphatic carbons although the acids may contains as few as eight aliphatic carbon atoms if the acid molecule includes an aromatic ring such as phenyl, naphthyl, etc. Representative organic acids are discussed and identified in detail in the above-noted patents. Particularly, U.S. Pat. Nos. 2,616,904 and 2,777,874 disclose a variety of very suitable organic acids. For reasons of economy and performance, oil-soluble carboxylic, sulfonic, and phenolic are particularly suitable.

Within the group of overbased carboxylic, sulfonic, and phenolic acids, the barium and calcium over-based mono-, di-, and tri-alkylated benzene and naphthalene (including hydrogenated forms thereof) petrosulfonic acids, higher fatty acids, and alkylated phenols are especially suitable. The petroleum sulfonic acids are a well-known class of materials which have been used as starting materials in preparing overbased products since the inception of overbasing techniques as illustrated by the above patents.

The overbased organic complexes used in the stabilizer systems of the invention usually contain from about 10 to about 70 percent by weight of metal containing components. The exact nature of these metal containing components is not known. Furthermore, the overbased organic complexes may be in colloidal non-Newtonian form as disclosed and described in U.S. Pat. No. 3,384,586 in contrast to single phase homoegeneous systems. However, this depends upon the reaction conditions and the choice of reactants in preparing the overbased materials. Sometimes there are present in the product insoluble contaminants. These contaminants are normally unreacted basic materials such as calcium oxide, barium oxide, calcium hydroxide, barium hydroxide or other metal base materials used as reactants in preparing the overbased material. It should be understood however, that the removal of these contaminants is not absolutely essential to the performance of this invention.

The metal compounds used in preparing the organic overbased complexes are the basic salts of metals in Group I and Group II-a of the Periodic Table such as Na, K, Ca, Ba, Mg and Sr. The anionic portion of the salt can be hydroxyl, oxide, carbonate, bicarbonate, sulfite, sulfide, sulfate, as disclosed in the above cited patents.

The preferred overbased organic complexes are those overbased with $CaCO_3$ and $BaCO_3$; especially preferred is $BaCO_3$.

The stabilizer composition of this invention can be used over a range of about 0.05 to about 10 phr (that is, parts by weight per 100 parts) of halogenated resin. The preferred range is about 0.25 to about 5.0 phr.

Alkali metal and alkaline earth metal salts of mercaptans and mercapto acids which may be incorporated in the composition of this invention are described in co-pending U.S. application Ser. No. 799,862 filed May 23, 1977 now abandoned which is incorporated herein by reference. The above mentioned application describes the metal salts by the formulas:

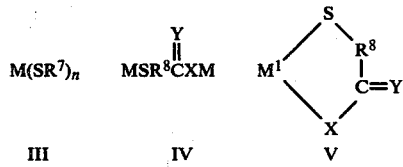

$$M(SR^7)_n \qquad \underset{\text{IV}}{MSR^8\overset{\overset{Y}{\|}}{C}XM} \qquad \underset{\text{V}}{M^1}$$

wherein:

M is a group IA metal (an alkali metal, in which case $n=1$) or a group IIA metal (an alkaline earth metal, in which case $n=2$);

$M^1$ is a group IIA metal;

$R^7$ is a hydrocarbon radical (such as alkyl, cycloalkyl, aryl, or mixed alkyl-aryl) of 1–22 carbon atoms, optionally substituted by halogen, —XH, —$XR^5$,

$$-X-\overset{\overset{Y}{\|}}{C}R^5, \text{ or } -\overset{\overset{Y}{\|}}{C}XR^5$$

where $R^5$ is a 1–20 carbon atom alkyl, alkenyl, cycloalkyl, aryl, or mixed alkyl-aryl group;

X and Y are independently selected from O and S;

and $R^8$ is a hydrocarbon linking group of 1–5 carbon atoms (which may be part of a cyclic structure) and is optionally substituted with halogen, —XH, —$XR^5$, $$-X-\overset{\overset{Y}{\|}}{C}R^5, \text{ or } -\overset{\overset{Y}{\|}}{C}XR^5$$

where $R^5$ is as described above

In the preparation of compounds of structure V there might be formed "polymeric" linear salts of the same empirical formula and these mixtures are operable and included in this invention.

Compositions containing more than one metal, and compositions having mixed R groups, are also operable and part of this invention.

The preferred metal salts of mercaptans or mercaptoacids which are optionally employed in this invention are the alkaline earth metal salts:

| | |
|---|---|
| $Ca(SCH_2CO_2C_8H_{17})_2$ | $Ca(SC_{12}H_{25})_2$ |
| $Ca(SCH_2CH_2CO_2C_8H_{17})_2$ | 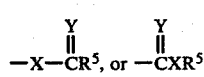 |
| $Ba(SC_{12}H_{25})_2$ | |
| $Ba(SCH_2CO_2C_8H_{17})_2$ | $Ca(SCHCO_2C_4H_9)_2$ |
| | $\quad\mid$ |
| | $CH_2CO_2C_4H_9$ |
| $Ba(SCH_2CH_2CO_2C_8H_{17})_2$ | $Ba(SCH_2CH_2O_2CC_{17}H_{33})_2$ |
| | $Ba(SCH_2CH_2O_2CC_{17}H_{35})_2$ |
| | $Ca(SCH_2CH_2O_2CC_{17}H_{33})_2$ |
| $Ba(SCHCO_2C_4H_9)_2$ | $Ca(SCH_2CH_2O_2CC_{17}H_{35})_2$ |
| $\quad\mid$ | |
| $CH_2CO_2C_4H_9$ | |

Especially preferred because of their superior performance are the following barium and calcium salts:

| | |
|---|---|
| $Ba(SCH_2CO_2C_8H_{17})_2$ | $Ba(SCH_2CH_2CO_2C_8H_{17})_2$ |
| $Ba(SCH_2CH_2O_2CC_{17}H_{33})_2$ | $Ba(SCH_2CH_2O_2OC_{17}H_{35})_2$ |
| $Ca(SCH_2CO_2C_8H_{17})_2$ | $Ca(SCH_2CH_2CO_2C_8H_{17})_2$ |
| $Ca(SCH_2CH_2O_2CC_{17}H_{33})_2$ | $Ca(SCH_2CH_2O_2CC_{17}H_{35})_2$ |

The three components are generally used in the weight percent amounts as follows:

| Wt. % | |
|---|---|
| 20–80 | tin tetrakis (mercaptide) |
| 20–80 | overbased organic complex of an alkali or alkaline earth metal base |
| 0–50 | alkali or alkaline earth metal salt of a |
| 100 | mercaptan or a mercaptoacid |

Preferred weight percent ranges are as follows:

| WT. % | |
|---|---|
| 25–70 | tin tetrakis (mercaptide) |
| 20–80 | overbased organic complex of an |

| WT. % | |
|---|---|
| | alkali or alkaline earth metal base |
| 0 or 5-40 | alkali or alkaline earth metal salt of |
| 100 | a mercaptan or a mercaptoacid |

As described in U.S. Pat. No. 3,925,309, the novel stabilizer compositions of this invention can be used with halogen containing vinyl and vinylidene resins in which the halogen is attached directly to the carbon atoms.

As the halogen resin there can be employed chlorinated polyethylene having 14 to 75%, e.g. 27% chlorine by weight, polyvinyl chloride, polyvinylidene chloride, polyvinyl bromide, polyvinyl fluoride, polyvinylidene fluoride, copolymers of vinyl chloride with 1 to 90%, preferably, 1 to 30% of a copolymerizable ethylenically unsaturated material e.g., vinyl acetate, vinyl butyrate, vinyl benzoate vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-1-chloroethylene, acrylonitrile, chloroacrylonitrile, allylidene diacetate and chloroallylidene diacetate. Typical copolymers include vinyl chloride-vinyl acetate (96:4 sold commercially as (VYNW), vinyl chloride-vinyl acetate (87:13), vinyl chloride-vinyl acetate-maleic anhydride (86:13:1), vinyl chloride-vinylidene chloride (95:5), vinyl chloride-diethyl fumarate (95:5), vinyl chloride-trichloroethylene (95:5), vinyl chloride-2-ethylhexyl acrylate (80:20).

Preferably the resin is a vinyl halide resin, specifically, a vinyl chloride resin.

The stabilizer composition of the present invention can be incorporated with the resin by admixing in an appropriate mill or mixer or by any of the other well-known methods which provide for uniform distribution throughout the resin compositions. Thus, mixing can be accomplished by milling on rolls at 100°-160° C.

In addition to the novel stabilizers there can also be incorporated with the resin conventional additives such as plasticizers, conventional stabilizers, antioxidants pigments, fillers, dyes, ultraviolet light absorbing agents, densifying agents and the like as identified and in the amounts set forth in U.S. Pat. No. 3,925,309.

This invention will be further understood by reference to the following Examples which serve to illustrate, but not limit, the invention.

EXAMPLE 1

Preparation of Tin Tetrakis (isooctyl thioglycolate)

To a mixture of 81.7 g (0.4 mole) of isooctyl thioglycolate and 26.1 g (0.1 mole) of anhydrous stannic chloride dissolved in 250 ml of hexane, is added a solution of 40.5 g (0.4 mole) of triethylamine in 100 ml of hexane. The mixture is stirred at room temperature for three hours and then filtered. The filtrate is concentrated under reduced pressure to give 81.0 g (87.0% yield) of product. Infrared data is consistent with the assigned structure.

Anal. Calcd. for $C_{40}H_{76}O_8S_4Sn$: C, 51.6; H, 8.22; S, 13.8; Sn, 12.7. Found: C, 52.6; H, 8.37; S, 13.6; Sn, 11.4.

Example 2

Preparation of Tin tris (issooctyl thioglycolate)-mono (butyl mercaptide)

Following the procedure described in Example 1, except that a mixture of 9.01 g (0.1 mole) of n-butyl mercaptan and 61.3 g (0.3 mole) of isooctyl thioglycolate is used in place of the isooctyl thioglycolate, there is obtained 74.5 g (91.0% yield) of product. Infrared data is consistent with the assigned structure.

Anal. Calcd. for $C_{34}H_{60}O_6S_4Sn$: C, 49.9; H, 8.13; S, 15.7; Sn, 14.5. Found: C, 50.2; H, 8.29; S, 15.0; Sn, 13.0.

EXAMPLE 3

Preparation of Tin bis (isooctyl thioglycolate)-bis(butyl mercaptide)

Following the procedure described in Example 1, except that a mixture of 18.0 g (0.2 mole) of n-butyl mercaptide and 40.9 g (0.2 mole) of isooctyl thioglycolate is used in place of the isooctyl thioglycolate, there is obtained 53.1 g (75.4% yield) of product. Infrared data is consistent with the assigned structure.

Anal. Calcd. for $C_{28}H_{56}O_4S_4Sn$: C, 47.8; H, 8.02; S, 18.2; Sn, 16.9. Found: C, 48.3; H, 8.03; S, 17.5; Sn, 15.4.

EXAMPLE 4

Preparation of Barium Carbonate Dispersion (Overbased Organic Complex)

In a three necked, round-bottomed flask equipped with a mechanical stirrer, Dean-Stark trap, and a stopper, a stirred mixture of: 57 g of nitrated polyisobutylene, 133 g of a light paraffin oil; 50 g of isooctyl alcohol; 60.8 g (0.28 eq.) of p-nonylphenol; and 138.7 g (1.6 eq) of barium hydroxide monohydrate is heated to 150° and maintained at that temperature for five hours to drive off the water. Thereupon, the reaction mixture is gassed with carbon dioxide at a rate of 19 g/hr. for three hours at 150° C. The isooctyl alcohol and excess water is then vacuum stripped and the product filtered. The yield of product, a dark, viscous solution, is 341.3 g (84.5%)

Theory: Ba, 27.7%; $CO_3^{-2}$, 10.0%. Found: Ba, 23.1%; $CO_3^{-2}$, 8.45%.

EXAMPLES 5-18

In the following examples, a standard single-screw pipe formulation is used which contains 100 parts by weight of a polyvinyl chloride homopolymer (VC 100 PM, Borden Chemical Co.); 3.0 parts by weight of a processing aid which is an acrylic polymer consisting of 90% methyl methacrylate and 10% ethyl acrylate (K-120N, Rohm and Haas Co.); 0.5 parts by weight of a paraffin wax (Rosswax 165, F. B. Ross Co.); 0.2 parts by weight of a partially saponified ester wax (Wax, OP, American Hoechst Co.); 1.4 parts by weight of calcium stearate; 2.0 parts by weight of titanium dioxide; and stabilizer as indicated (all amounts in parts by weight). The resin mixtures are dryblended in a Waring Commercial Blender and their dynamic heat stability determined on a Brabender Plastograph using a 67.5 g charge, 415° F. stock temperature, and 40 rpm mixing head speed. The dynamic heat stability (failure time) of the polymer mixture is reported as the number of minutes from the point of polymer fusion to the onset of degradation.

TABLE 1

| Ex. No. | Parts | Stabilizer | Failure (Min.) |
|---|---|---|---|
| 5 | | None | 7 |
| 6 | 1.5 | Dibutyltin bis(isooctyl thioglycolate) | 21 |
| 7 | 1.5 | Tin tetrakis(isooctyl thioglycolate) | 4 |
| 8 | 0.75 | Tin tetrakis (isooctyl thioglycolate) | 3 |
| 9 | 0.75 | BaCO₃ Overbased Complex | 4 |
| 10 | 1.2 | Tin tetrakis(isooctyl thioglycolate) | 16 |
| | 0.3 | BaCO₃ overbased complex | |
| 11 | 0.75 | Tin tetrakis(isooctyl thioglycolate) | 22 |
| | 0.75 | BaCO₃ overbased complex | |
| 12 | 1.5 | Tin tris(isooctyl thioglycolate)mono(butyl mercaptide) | 3 |
| 13 | 1.2 | Tin tris(isooctyl thioglycolate)mono(butyl mercaptide) | 15 |
| | 0.3 | BaCO₃ overbased complex | |
| 14 | 0.75 | Tin tris(isooctyl thioglycolate)mono(butyl mercaptide) | 20 |
| | 0.75 | BaCO₃ overbased complex | |
| 15 | 1.5 | Tin bis(isooctyl thioglycolate)bis(butyl mercaptide) | 4 |
| 16 | 1.2 | Tin bis(isooctyl thioglycolate)bis(butyl mercaptide) | 16 |
| | 0.3 | BaCO₃ overbased complex | |
| 17 | 0.75 | Tin bis(isooctyl thioglycolate)bis(butyl mercaptide) | 21 |
| | 0.75 | BaCO₃ overbased complex | |
| 18 | 0.75 | Tin tetrakis(isooctyl thioglycolate) | 20 |
| | 0.60 | BaCO₃ overbased complex | |
| | 0.15 | Barium bis(isooctyl thioglycolate) | |

These results demonstrate the dramatic and unexpected synergistic effect resulting from the combination of tin tetrakis (mercaptides) with an overbased complex.

EXAMPLES 19–23

Examples of the advantageous effect the alkaline earth metal salts of mercaptides have on the color inhibiting performance of the stabilizer composition are given in Table 2. Performance tests are as described for Examples 5–18 except that samples are withdrawn from the Brabender at three minute intervals. The discoloration of the sample is rated visually and recorded, according to the following abbreviations.

| Color | Degree |
|---|---|
| G — Gray | L — Light |
| PK — Pink | P — Pale |
| W — White | V — Very |
| Y — Yellow | |

TABLE 2

| Example No. | Parts | Stabilizer | 3 | 6 | 9 | 12 | 15 |
|---|---|---|---|---|---|---|---|
| 19 | — | None | PK | G | — | — | — |
| 20 | 1.5 | Dibutyltin bis (isooctyl thioglycolate) | W | W | W | VPY | LY |
| 21 | 1.5 | Tin tetrakis (isooctyl thioglycolate) | G | — | — | — | — |
| 22 | 1.2 | Tin tetrakis (isooctyl thioglycolate) | W | W | VPY | VPY | G |
| | 0.3 | BaCO₃ overbased complex | | | | | |
| 23 | 1.0 | Tin tetrakis (isooctyl thioglycolate) | W | W | W | VPY | G |
| | 0.25 | BaCO₃ overboard complex | | | | | |
| | 0.25 | Barium bis (isooctyl thioglycolate) | | | | | |

(Time (Minutes) spans columns 3, 6, 9, 12, 15)

I claim:

1. A composition comprising a mixture of (a) from about 20 to 80 weight percent of a tin tetrakis (mercaptide) having the formula:

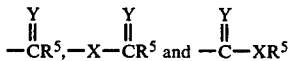

where
R¹, R², R³ and R⁴ are hydrocarbon radicals having from 1 to 22 carbon atoms and are independently selected from the group consisting of alkyl, cycloalkyl, aryl, mixed alkyl-aryl and said hydrocarbon radicals having a substituent selected from the group consisting of halogen, —XH, —XR⁵, $$-CR^5, -X-\overset{Y}{\underset{\|}{C}}R^5 \text{ and } -\overset{Y}{\underset{\|}{C}}-XR^5$$

where R⁵ is a hydrocarbon radical having from 1 to 20 carbon atoms and is selected from the group consisting of alkyl, alkenyl, cycloalkyl, aryl and mixed alkyl-aryl, and X and Y are independently either oxygen or sulfur; and (b) from about 80 to 20 weight percent of an overbased organic complex of an alkali or alkaline earth metal base having the formula $$R_n^6M.xM^1A_{n'}$$

where
R⁶ is a residue of an organic acid selected from the group consisting of carboxylic, thiocarboxylic, sulfonic, sulfinic, phosphonic, phosphinic, thiophosphonic, thiophosphinic, phenolic, and thiophenolic;
n and n' are independently 1 or 2;
M and M¹ are independently selected from the group consisting of alkali and alkaline earth metals; x is a positive integer greater than zero; and
A is an anion of the base material selected from the group consisting of OH⁻¹, CO₃⁻², O⁻², SO₄⁻², SO₃⁻², HCO₃⁻¹ and S⁻².

2. The composition of claim 1 additionally containing from about 1 to about 50 percent, based on the weight of the composition, of an alkali or alkaline earth metal salt of a mercaptan or a mercaptoacid having one of the following formulas:

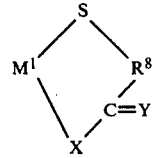

wherein
  M is an alkali or alkaline earth metal;
  $M^1$ is an alkaline earth metal;
  n is 1 when M is an alkali metal and n is 2 when M is an alkaline earth metal;
  $R^7$ is a hydrocarbon radical having 1 to 22 carbon atoms and is selected from the group consisting of alkyl, cycloalkyl, aryl, mixed alkyl-aryl and said hydrocarbon radical having a substituent selected from the group consisting of halogen, —XH, —$XR^5$,

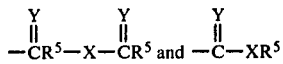

where $R^5$ is as described in claim 1;
X and Y are independently oxygen or sulfur;
$R^8$ is a divalent hydrocarbon linking group having from 1 to 5 carbon atoms or said hydrocarbon linking groups having a substituent selected from the group consisting of halogen, —XH, —$XR^5$,

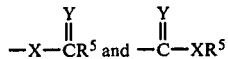

where $R^5$, X and Y are as described hereinabove.

3. The composition of claim 1 wherein $R^1$, $R^2$, $R^3$, and $R^4$ are independently selected from the group consisting of —$C_4H_9$, —$C_{12}H_{25}$, —$CH_2CO_2R^5$, —$CH_2CH_2CO_2R^5$ and —$(CH_2)_zO_2CR^5$ where $R^5$ is as described in claim 3 and z is an integer of from 1 to 3.

4. The composition of claim 1 wherein the tin tetrakis (mercaptide) is selected from the group consisting of

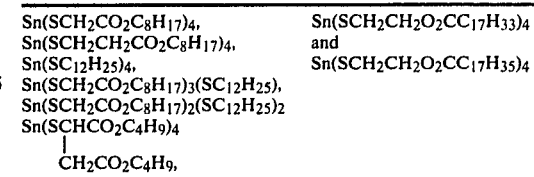

5. The composition of claim 4 wherein the overbased organic complex is overbased with $BaCO_3$ or $CaCO_3$ and the alkaline earth metal salt of a mercaptan or mercaptoacid is selected from the group consisting of $Ba(SCH_2CO_2C_8H_{17})_2$, $Ba(SCH_2CH_2CO_2C_8H_{17})_2$, $Ba(SCH_2CH_2O_2CC_{17}H_{33})_2$, $Ba(SCH_2CH_2O_2CC_{17}H_{35})_2$, $Ca(SCH_2CO_2C_8H_{17})_2$, $Ca(SCH_2CH_2CO_2C_8H_{17})_2$, $Ca(SCH_2CH_2O_2CC_{17}H_{33})_2$ and $Ca(SCH_2CH_2O_2CC_{17}H_{35})_2$.

6. The composition of claim 1 dispersed in a halogenated resin.

7. The composition of claim 2 dispersed in a halogenated resin.

8. The composition of claim 1 dispersed in poly(vinyl chloride)resin.

9. The composition of claim 2 dispersed in poly(vinyl chloride) resin.

10. The composition of claim 4 dispersed in a resinous homopolymer or copolymer of vinyl chloride.

11. The composition of claim 5 dispersed in a resinous homopolymer or copolymer of vinyl chloride.

* * * * *

UNITED STATES PATENT OFFICE
CERTIFICATE OF CORRECTION

Patent No. 4,177,187      Dated December 4, 1979

Inventor(s) Joseph M. Bohen

It is certified that error appears in the above-identified patent and that said Letters Patent are hereby corrected as shown below:

1. In column 10, claim 2, line 5 after "following formulas:" The following formulas should appear $M(SR^7)_n$, $MSR^8\overset{Y}{\underset{\|}{C}}XM$, 2. In column 5, line 40, after "1977" the word "abandoned" should be replaced with ---Patent No. 4,115,352 issued September 19, 1978.

Signed and Sealed this

Nineteenth Day of August 1980

[SEAL]

Attest:

SIDNEY A. DIAMOND

*Attesting Officer*     *Commissioner of Patents and Trademarks*